US00PP11459P

United States Patent [19]

Heims

[11] Patent Number: Plant 11,459

[45] Date of Patent: Jul. 25, 2000

[54] SILENE DIOICA PLANT NAMED 'JADE VALLEY'

[75] Inventor: Dan M. Heims, Portland, Oreg.

[73] Assignee: Terra Nova Nurseries, Inc., Portland, Oreg.

[21] Appl. No.: 09/073,503

[22] Filed: May 5, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Wendy A. Baker
*Attorney, Agent, or Firm*—Klarquist Sparkman Campbell Leigh & Whinston, LLP

[57] ABSTRACT

A new and distinct *Silene dioica* plant characterized by unusual jade-green centers on cream-color leaves.

2 Drawing Sheets

The present invention relates to a new and distinct sport of *Silene dioica* 'Graham's Delight' (unpatented) in the family Caryophyllaceae (the Carnation family) which originated in tissue culture.

The new Silene is a result of a sport that occurred at Terra Nova Nurseries, Inc., in Canby, Oreg. This sport was found in tissue culture from a jar of *Silene dioica* 'Graham's Delight' (unpatented), a streaked form. The original plant was retained to observe habit and to compare with their ensuing multiplying shoots. The new variety has been reproduced only by asexual propagation (division and tissue culture). Each of the progeny exhibits identical characteristics to the original plant and is unlike any *Silene dioica* offered by any American nursery as evidenced by the following characteristics:

Cream-color leaves with a jade-green patch at the leaf center. Asexual propagation by division and tissue-culture as done in Tigard, Oreg., shows that the foregoing characteristics and distinctions come true to form and are established and transmitted through succeeding propagations.

DETAILED PLANT DESCRIPTION

Figure 1:
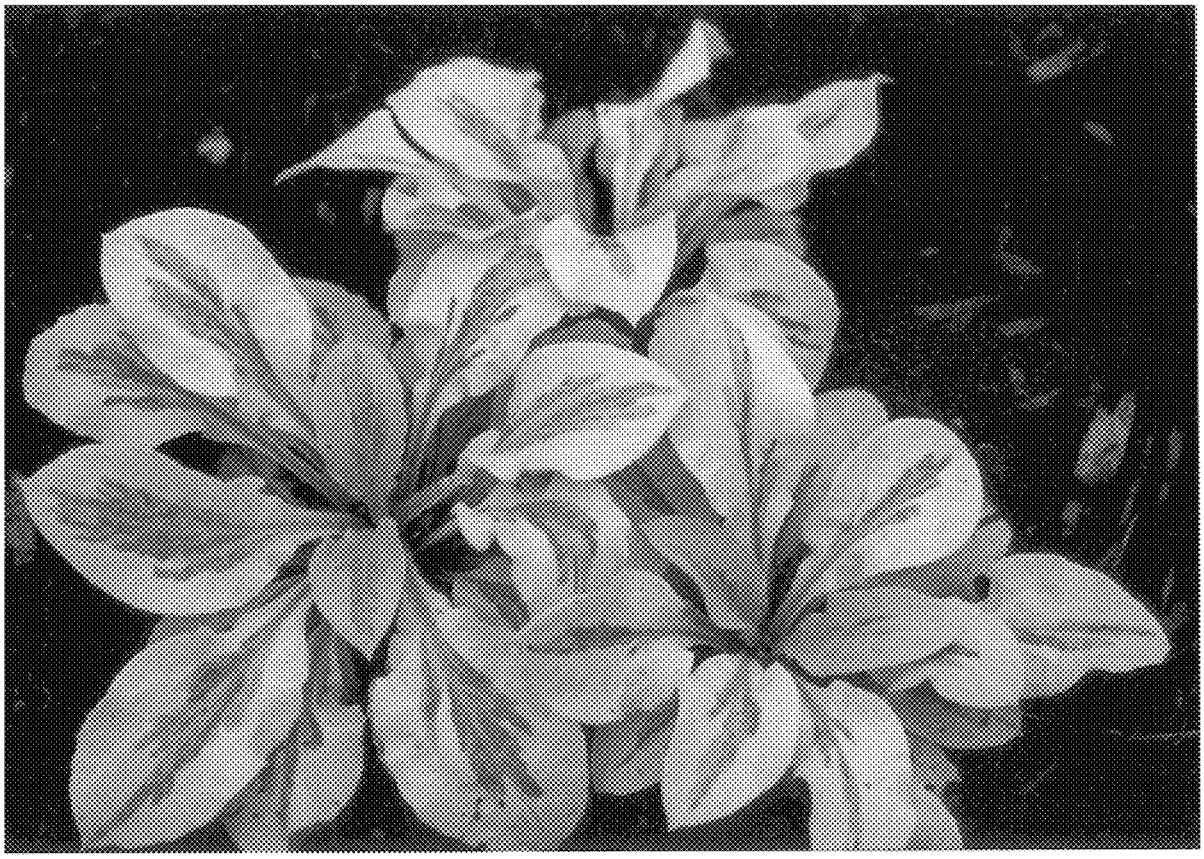
FIG. 1 shows three young plants in April.
Figure 2:
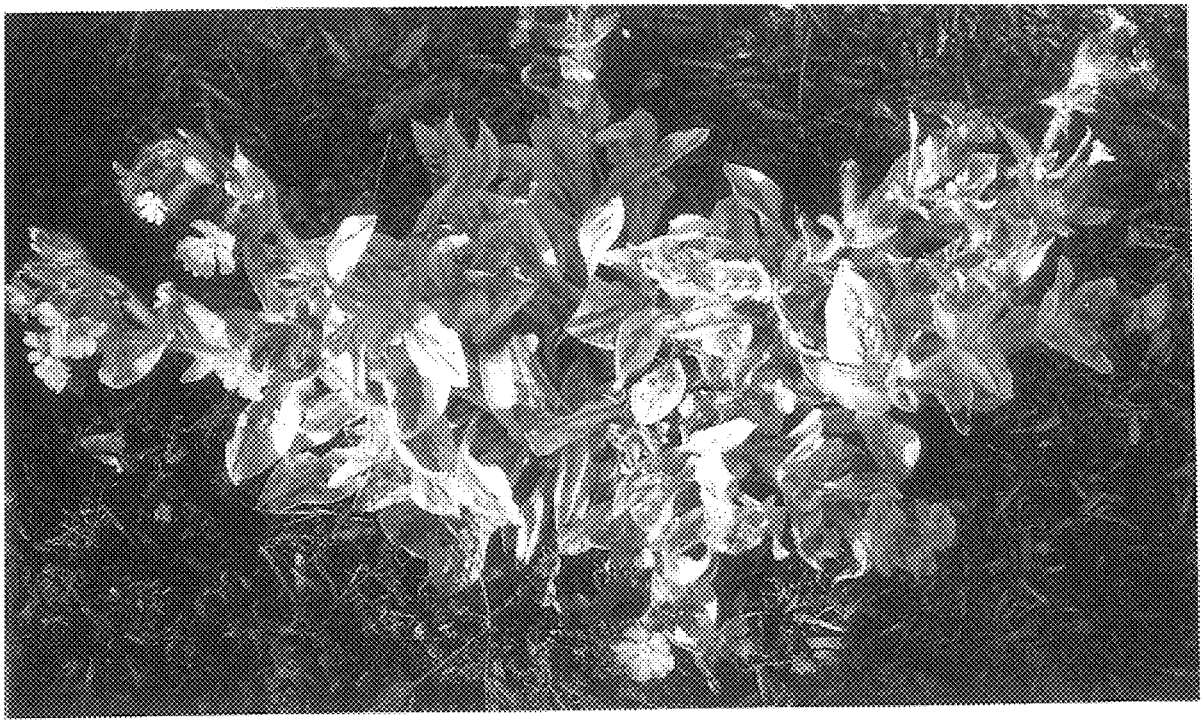
FIG. 2 shows the flowers in bloom.

The following is a detailed description of the new Silene selection in Canby, Oreg. The color descriptions are all based on The Royal Horticultural Society Colour Chart and The American Rhododendron Society publication: "A Contribution Toward Standardization of Color Names in Horticulture."

Foliage:
- *Type.*—Herbaceous.
- *Shape.*—Oblanceolate.
- *Length.*—16.5–17.5 cm.
- *Width.*—6–7 cm.
- *Petiole length.*—5.5–6.5 cm.
- *Margins.*—Entire.
- *Apex.*—Acute.
- *Base.*—Attenuate.
- *Texture.*—Minutely hairy.
- *Leaf arrangement.*—Basal clump.
- *Venation.*—Camptodromus.

Size:
- *Height.*—10 cm (1-year- old plant grown in Canby, Oreg.).
- *Width.*—25 cm (1-year- old plant grown in Canby, Oreg.).

Flower: Note: Silene 'Jade Valley' is a male clone; the species is *dioecious.*
- *Petal count.*—5
- *Petal shape.*—2-lobed, obovate.
- *Flower type.*—(Male) calyx tubular, inflated; stamens exserted.
- *Flower size.*—1.5–2 cm (0.75–1 in).
- *Flower number.*—20–25 flowers per panicle.
- *Flower stem texture.*—Pubescent.
- *Flower stem width.*—5 mm tapering to 1.5 mm.
- *Blooming habit.*—Paniculate up to 25 cm (10 in). No tendency towards fasciation observed.
- *Bloom period.*—Early April for 6–8 weeks following (in Oregon).

Disease: Susceptible to root rot when grown under wet condition.

Color characteristics:
- *Foliage.*—Mature leaves upper surface — spring: R.H.S. 10B-7B Yellow Group (Brilliant Yellow ARS) with green markings R.H.S. 137A (Moderate Olive Green ARS). Upper surface — summer through winter: R.H.S. 136A Green group (Dark Green ARS), lightening to R.H.S. 133 A-C Green group (Dark Bluish Green to Light Bluish Green ARS) to R.H.S. 151A Yellow-Green group (Strong Greenish Yellow ARS). Lower surface: R.H.S. 138A Green group (Moderate Yellowish Green ARS) to R.H.S. 144B Yellow Green group (Strong Yellow Green ARS) to R.H.S. 151A Yellow Green group (Strong Greenish Yellow ARS).
- *Flowers.*—R.H.S. 73A Red Purple Group (Deep Purplish Pink ARS).
- *Flower stems.*—R.H.S. 147C Yellow Green Group.

DESCRIPTION OF PARENT PLANT

*Silene dioica* is a green-leaved plant native to England. Flowers are showy and rose-pink in color. *Silene dioica* 'Graham's Delight' (unpatented) is a streaked variegated cultivar of *Silene dioica*. Whereas the instant plant exhibits periclinal variegation, in which phenotypic expression is that of a creamy-yellow leaf with a green center, *Silene dioica* 'Graham's Delight' exhibits sectorial variegation, in which phenotypic expression is that of a green leaf with unorganized creamy-yellow sectorial streaks throughout.

I claim:

1. A new and distinct *Silene dioica* plant substantially as shown and described, characterized by its unusual jade-green centers on cream-color leaves.

* * * * *